United States Patent [19]

Welter et al.

[11] Patent Number: 5,342,371
[45] Date of Patent: Aug. 30, 1994

[54] HELICAL SURGICAL SNARE

[75] Inventors: Lawrence H. Welter, Oakland, Calif.; Scott D. Downey; Todd A. Hall, both of Bloomington, Ind.

[73] Assignee: Cook Incorporated, Bloomington, Ind.

[21] Appl. No.: 158,008

[22] Filed: Nov. 24, 1993

[51] Int. Cl.$^5$ .............................................. A61B 19/00
[52] U.S. Cl. ..................................... 606/113; 606/108
[58] Field of Search .................... 606/1, 32, 34, 37, 39, 606/40, 45, 46, 47, 49, 50, 106, 108, 110, 113, 114, 127, 167, 170, 205–209

[56] References Cited

U.S. PATENT DOCUMENTS

| | | | |
|---|---|---|---|
| 3,491,747 | 8/1966 | Robinson . | |
| 3,507,270 | 4/1970 | Ferrier . | |
| 3,791,387 | 2/1974 | Itoh | 606/113 |
| 4,326,530 | 4/1982 | Fleury, Jr. . | |
| 4,790,812 | 12/1988 | Hawkins, Jr. et al. | 604/22 |
| 5,108,406 | 4/1992 | Lee | 606/106 |
| 5,163,938 | 11/1992 | Kambara et al. | 606/47 |
| 5,192,286 | 3/1993 | Phan et al. | 606/106 |

OTHER PUBLICATIONS

Bilbao, Marcia K. et al. "Catheter Retrieval of Foreign Body from the Gastrointestinal Tract", *Am. J. Roentgenol., Rad. Therapy & Nuclear Med.* Mar. 1971, vol. III, No. 3, 473–475.
Dotter, Charles T. et al. "Transluminal Extraction of Catheter and Guide Fragments from the Heart and . . . ", *Am J. Roentgenol., Rad. Therapy & Nuclear Med.,* Mar. 1971, vol. III, No. 3, 467–472.
Graham, K. J. et al. "Catheter Emboli to the Heart and Pulmonary Artery", *Brit. J. Surg.,* Mar. 1970, vol. 57, No. 3, 184–186.
Mather, A. P. et al. "Fogarty Balloon Catheter for Removal of Catheter Fragment in Subclavian Vein", *JAMA,* Jul. 1971, vol. 217, No. 4, 481.
McSweeney, William J. et al. "Retrieval of a Catheter Foreign Body from the Right Heart Using a Guide Wire Deflector System", *Radiology,* Jul. 1971, vol. 100, 61–62.
Microvena Corp., "Amplatz 'Goose-Neck' Snare", Vadnais Heights, Minn.
Miller, Roscoe E. et al. "Percutaneous Removal of Catheter Emboli", *JAMA,* Oct. 1970, vol. 214, No. 3, 589–590.
Miller, Roscoe E. et al. "Removal of intravascular and endobronchial foreign bodies by nonoperative snare technique", *Surgery,* Mar. 1971, vol. 69, No. 3, 463–468.
Nash, Gerald et al. "Paradoxical Catheter Embolism", *Arch. Surg.,* Mar. 1971, vol. 102, 213.
Ramo, Barry W. et al. "Migration of a Severed Transvenous Pacing Catheter and Its Successful Removal", *American Journal of Cardiology,* Dec. 1968, vol. 22, 880–884.
Rossi, Plinio. "'Hook Catheter,' Technique for Transfemoral Removal of Foreign Body from Right Side . . . ", *Am. J. Roentgenol., Rad. Therapy & Nuclear Med.,* May 1970, vol. 109, No. 1, 101–106.

(List continued on next page.)

*Primary Examiner*—Stephen C. Pellegrino
*Assistant Examiner*—Glenn K. Dawson
*Attorney, Agent, or Firm*—Richard J. Godlewski

[57] ABSTRACT

A helical surgical snare (10) for engaging and capturing a foreign body for example in the vascular system of a human or animal body. The helical surgical snare includes an elongated tubular member (11) with the distal portion (34) of a filament wire (17) wrapped around the exterior surface (15) of the distal portion of the tube. The filament wire is positioned within the passage (14) of the tubular member and exits about the distal portion (25) thereof via inclined side ports. The distal end (18) of the filament wire is attached in the passage to the distal end (13) of the tubular member. A helical snare loop (19) is formed externally around the tubular member between the two side ports (16, 20). A handle (30) positioned at the proximal end of the tubular member pushes and pulls the distal portion of the filament wire to operate the snare loop between various open and collapsed positions.

20 Claims, 3 Drawing Sheets

OTHER PUBLICATIONS

Samaan, H. A. "Intracardiac Foreign Bodies", *Brit. J. Surg.*, Sep. 1970, vol. 57, No. 9, 685–687.

Silver, Walter et al. "Intracardiac Catheter as a Foreign Body of Six Years' Duration Resulting in Endocarditis", *Chest*, Mar. 1971, vol. 59, No. 3, 344–346.

Smyth, Nicholas P. D. et al. "Transjugular removal of foreign body from the right atrium by . . . ", *Journal of Thoracic and Cardiovascular Surgery*, Apr. 1963, vol. 55, No. 4, 594–597.

Smyth, Nicholas P. D. et al. "Transvenous Removal of Catheter Emboli from the Heart and Great Veins by Endoscopic Forceps", *Annals of Thoracic Surgery*, May 1971, vol. 11, No. 5, 403–408.

Weisse, Allen B. "Snaring of a Broken Sommer Pacemaker Electrode", *Annals of Internal Medicine*, 1970, vol. 72, No. 5, 695–697.

Wellmann, Klaus F. et al. "Polyethylene Catheter Embolism", *Circulation*, Mar. 1968, vol. 37, 380–392.

Yedlicka, Joseph W., Jr., et al. "Nitinol Gooseneck Snare for Removal of Foreign Bodies", *Radiology*, 1991, vol. 178, 691–693.

Henley, Felix T., M.D. et al., "Percutaneous Removal of Flexible Foreign Body from the Heart," *Technical Notes*, Jan. 1969, vol. 92, p. 176.

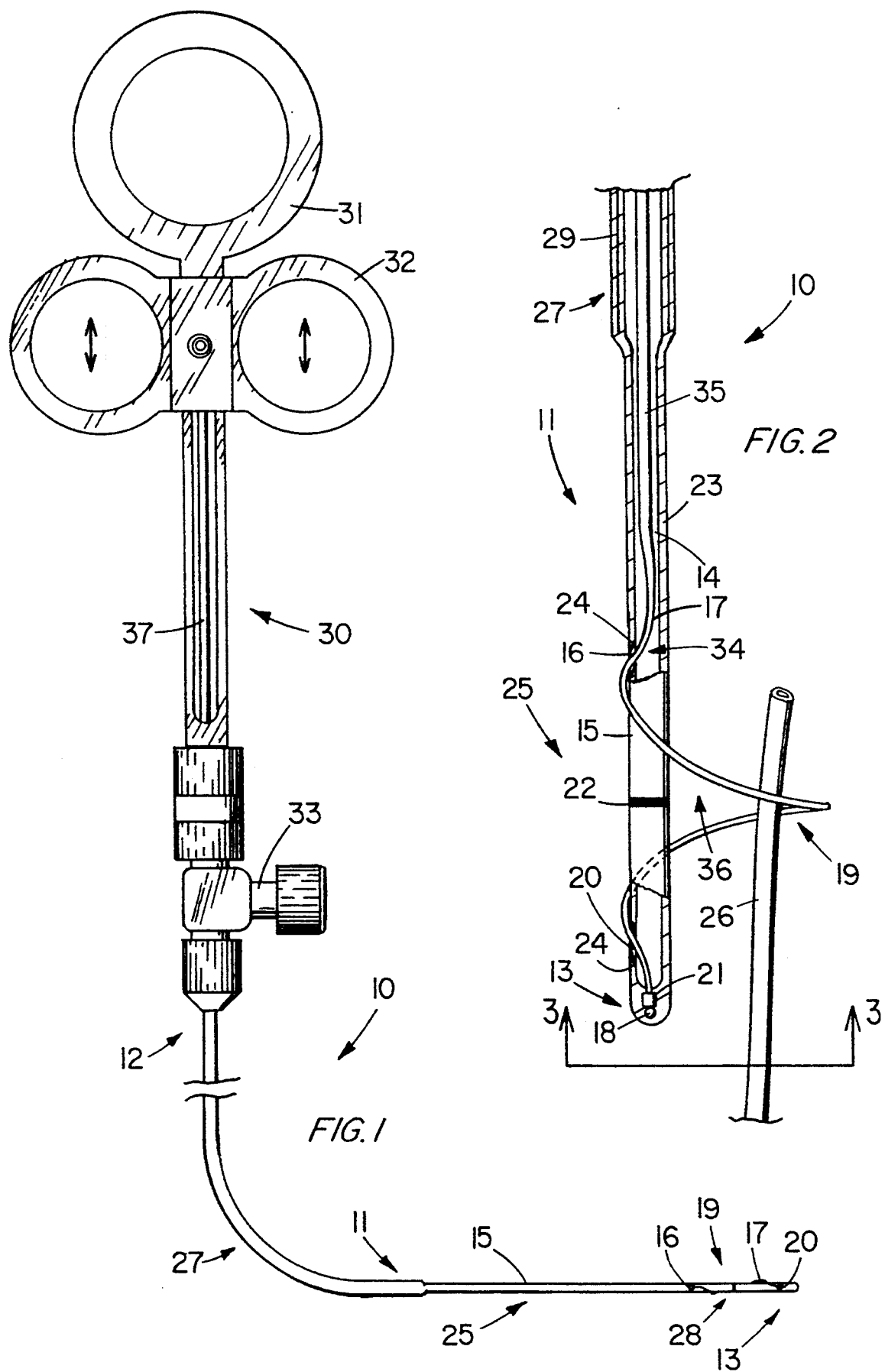

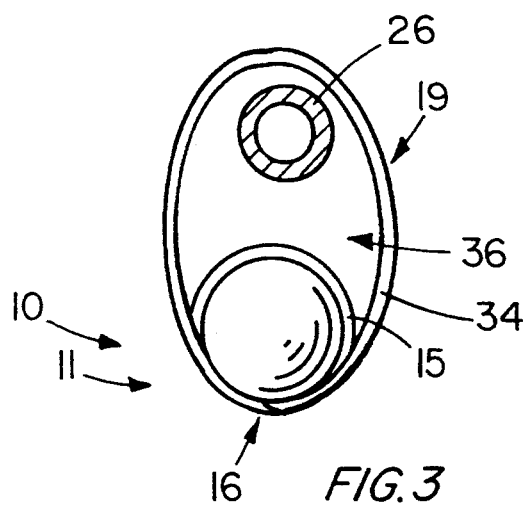
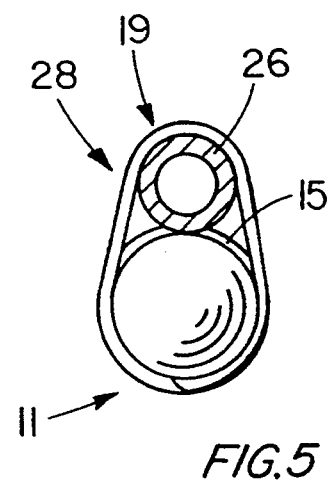
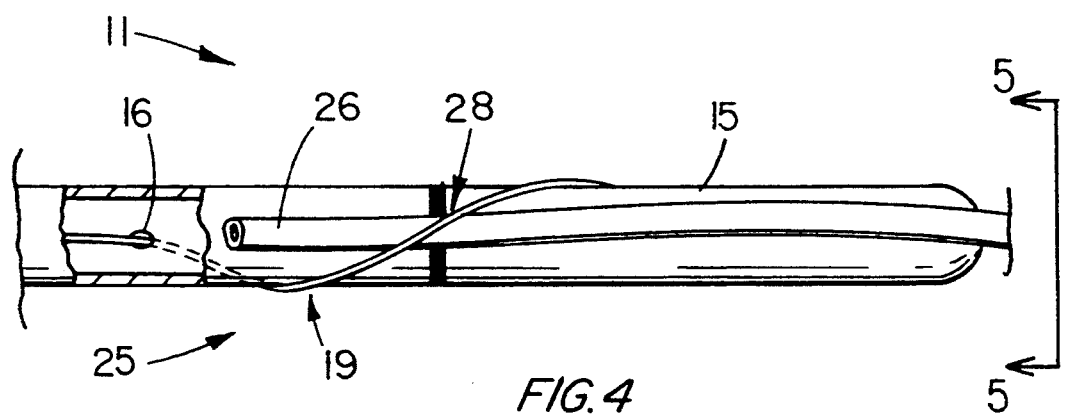

HELICAL SURGICAL SNARE

TECHNICAL FIELD

This invention relates generally to surgical snares and, in particular, to a helical surgical snare for retrieving foreign bodies from, for example, the vascular system of a human or animal body.

BACKGROUND OF THE INVENTION

The use of catheters, wire guides, pacemaker leads, and other medical devices in the vascular system of a patient often results in the breakage or fragmentation of the device. Once broken or fragmented, a fragment of the device is released in the vascular system of a patient. Even simple, routine procedures such as intravenous infusion and pressure monitoring can result in a fragment or foreign body being released in the bloodstream of a patient. This foreign body typically moves through the bloodstream and potentially causing a number of clinical complications including sepsis, perforation, thrombosis, arrhythmias, myocardial necrosis, and death. Therefore, it is necessary and urgent to remove the foreign body from the vascular system of a patient.

One approach to removing a foreign body from the vascular system of a patient is to perform open surgery, which is costly, traumatic, requires long periods of healing and recovery, and implies a further risk of complications. If the foreign body is positioned in a branch of a pulmonary artery, for example, a thoracotomy procedure is required. As a result, a patient who has only undergone a routine vascular access procedure for testing or diagnosis can be required to undergo major surgery due to a complication.

Another approach to removing a foreign body from the vascular system of a patient is the use of a retrieval device during a minimally invasive vascular access procedure typically performed with a visualization aid such as fluoroscopy. Several retrieval devices are proposed for this use. One proposed retrieval device has a distal hook. The distal hook is positioned centrally along the length of an elongated fragment or foreign body for grasping the fragment. Then the retrieval device is pulled so that the fragment is dragged through the vascular system and out of the patient's body. A limitation of this device is that the hook cannot grasp and pull a very short fragment or foreign body. A problem with this device is that it grasps the fragment in a transverse orientation with respect to the axis of the retrieval device. As a result, the fragment extends from the hook at an angle, which makes manipulation through the tortuous vessels of the vascular system problematic. The transversely extending fragment potentially traumatizes and catches on blood vessel walls. Another problem with the use of this device is that the elongated fragment trails the hook in a doubled strand during travel through the tortuous vascular system. As a result, the fragment causes significant drag or friction so that the fragment slides out of the hook and, again, traumatizes blood vessel walls.

Another retrieval device has a distal loop or snare for being positioned over one end of an elongated fragment and tightened thereabout. A problem with this device is that it grasps an elongated fragment transversely with respect to the axis of the retrieval device. Again, the transversely extending foreign body potentially traumatizes blood vessel walls during travel through the vascular system of the patient. Furthermore, the foreign body can become caught or wedged in the tortuous vessels and require surgical removal. Another problem with a distal loop is that the loop wire can be easily kinked during engagement of the fragment. As a result, the snare is often rendered ineffective and should be replaced.

Another retrieval device has a pair of distally positioned forceps jaws for grasping a foreign body anywhere along the length thereof. A problem with this device is that the narrow, tortuous vessels of the vascular system offer limited space for the forceps jaws to open and close. Another problem with this device is that the jaws are typically used to grasp the central portion of an elongated fragment. As a result, the fragment has a transverse orientation with respect to the axis of the retrieval device. Again, the problems of traumatizing vessel walls and inadvertently releasing the fragment from the retrieval device are presented.

SUMMARY OF THE INVENTION

The foregoing problems are solved and a technical advance is achieved in an illustrative helical surgical snare for withdrawing a foreign body or fragment from, for example, the vascular system of a human or animal body with a minimum of trauma thereto. The helical surgical snare comprises an elongated member with a passage extending longitudinally therethrough with a side port positioned in an exterior surface proximate the distal end thereof for external communication with the passage. A filament extends through and is moveable within the passage and side port and has a distal end attached to the elongated member. The distal portion of the filament is advantageously wrapped around the exterior surface of the elongated member and forms a helical snare loop external to the elongated member. The loop is opened for engaging a foreign body when the filament is moved through the side port and away from the exterior surface of the elongated member. The loop is closed to capture a foreign body when the filament is moved through the side port and toward the exterior surface of the elongated member.

The elongated member of the helical surgical snare advantageously includes a second port that is positioned distally from the first port and communicates with the passage therein. The distal portion of the filament extends through the first side port, wraps around the exterior surface of the elongated member, and reenters the member through a second side port to form the helical snare loop. The distal end of the filament is advantageously attached in the passage to the distal end of the elongated member. To radiographically visualize the distal end of the filament and elongated member, a radiopaque marker is positioned at the distal end of the filament. A radiopaque marker is also positioned between the first and second side ports to radiographically visualize the position of the helical snare loop apex. The side ports are inclined through the wall of the elongated member at a predetermined angle to advantageously facilitate ease of the operation of the snare loop between open and collapsed positions.

The elongated member of the snare includes a distal portion having a cross-sectional dimension and a proximal portion having a cross-sectional dimension greater than the cross-sectional dimension of the distal portion. The distal portion of the filament wire is wrapped around the exterior surface of the distal portion of the elongated member and has a collapsed position against the exterior surface thereof wherein the combined cross-sectional dimension of the wire and distal tubular portion approximates the cross-sectional dimension of the proximal tubular portion. This advantageously minimizes trauma to the vascular system of a human or animal body when introducing and withdrawing the snare.

The proximal portion of the elongated tubular member advantageously includes a wire braided in the wall of the tube to facilitate directional control of the snare through the vascular system of the patient.

The snare also includes a handle having first and second movable pieces connected to the proximal ends of the tubular member and filament wire for operating the helical snare loop between the various open and collapsed positions.

A side port connector is advantageously positioned at the proximal end of the tubular member for injecting contrast medium to radiographically visualize the capture area.

BRIEF DESCRIPTION OF THE DRAWING

FIG. 1 depicts an illustrative embodiment of a helical surgical snare of the present invention;

FIG. 2 depicts an enlarged and partially sectioned side view of the helical snare loop of FIG. 1 in an open position for engaging and capturing a foreign body;

FIG. 3 depicts a partially sectioned end view of the helical surgical snare and foreign body of FIG. 2 taken along the line 3—3;

FIG. 4 depicts an enlarged and partially sectioned bottom view of the helical surgical snare of FIG. 1 with the helical snare loop thereof in a partially collapsed position capturing the foreign body;

FIG. 5 depicts an end view of the helical surgical snare and the captured foreign body of FIG. 4 taken along the line 5—5.

DETAILED DESCRIPTION

Figure 6:
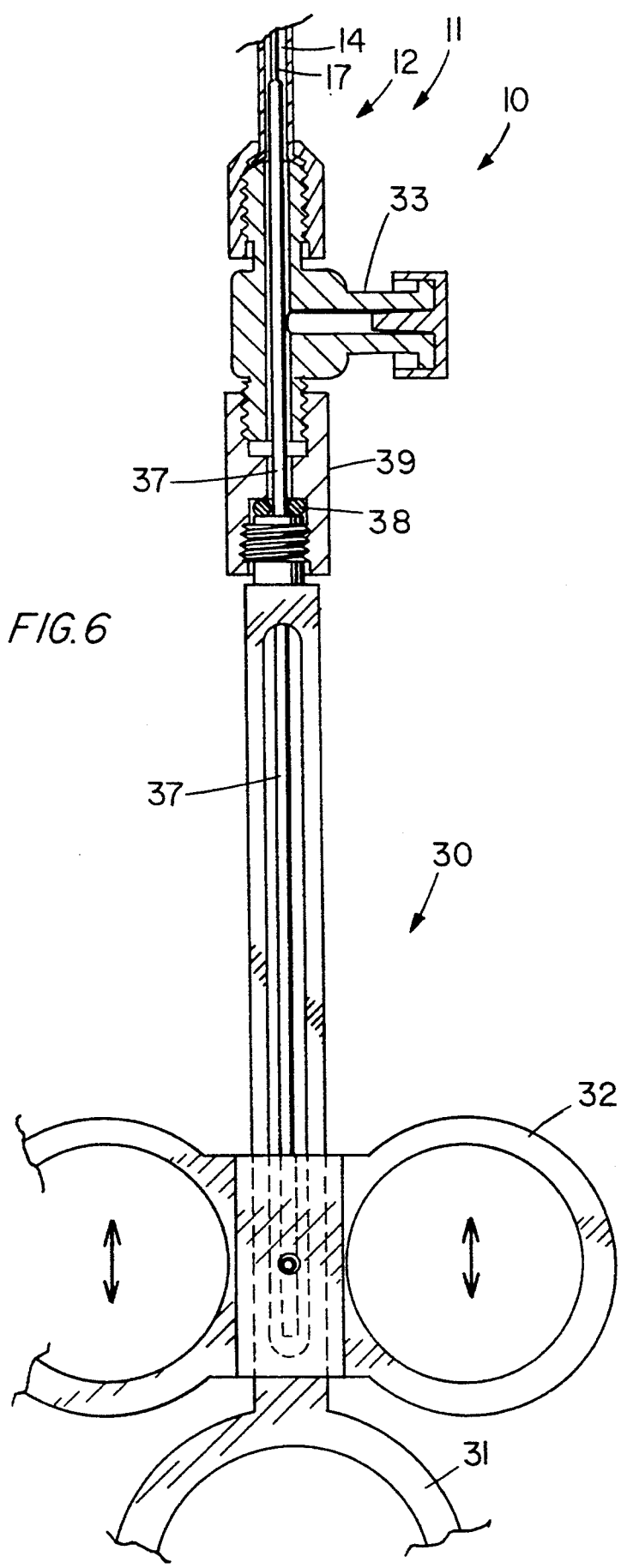
FIG. 6 depicts an enlarged and partially sectioned top view of the helical surgical snare of FIG. 1 and, in particular, the proximal end thereof with a handle connected thereto.

Depicted in FIG. 1 is an illustrative embodiment of helical surgical snare 10 for removing a foreign body or medical device fragment from, for example, the intravascular system of a human or animal body. The helical surgical snare comprises elongated tubular member 11 with a filament wire 17 helically wrapped around exterior surface 15 near distal end 13 of the tubular member, thus forming helical snare loop 19. Depicted in fully collapsed position 28 against exterior surface 15 of the tubular member between side ports 16 and 20, the helical loop is extended radially from the tubular member to an open position for engaging and capturing a foreign body or fragment therein.

FIG. 2 depicts an enlarged and partially sectioned side view of helical snare loop 19 of FIG. 1 in open position 36 for engaging and capturing therein foreign body or medical device fragment 26. The helical loop is extended radially from exterior surface 15 of the elongated member to open position 36 when distal portion 34 of filament wire 17 is moved through side port 16 with the assistance of handle 30.

As depicted in FIG. 1, handle 30 includes thumb and finger pieces 31 and 32. Stationary thumb piece 31 is connected to proximal end 12 of elongated tubular member 11 via side port connector 33. Slidable ring piece 32 is connected to the proximal end of filament wire 17 via stiffening cannula 37. The filament wire extends the entire length of tubular member 11, out proximal member end 12, longitudinally through side port connector 33, and attaches to slidable ring piece 32 via stiffening cannula 37.

To operate the helical snare loop between open and collapsed positions, the physician places his index and middle fingers in slidable ring handle piece 32 and his thumb in stationary thumb handle piece 31 and slides the two handle pieces relative to each other. To capture a foreign body within, for example, the vascular system of a patient, the helical snare loop is percutaneously inserted into a vessel adjacent the foreign body and moved to the open position by sliding the finger handle piece forward. Distal portion 34 of filament wire 17 is extended through side port 16, thereby radially expanding helical snare loop 19 to an open position. The elongated tubular member is advanced further into the vessel to position the foreign body within the helical snare loop. When the foreign body is so positioned, the snare loop is collapsed by the physician sliding the finger handle piece backwards toward the thumb piece, thereby drawing the foreign body or fragment against exterior surface 15 of the tubular member.

Helical surgical snare 10 engages and captures the foreign body or fragment without laterally deforming or kinking snare loop 14 or distal end 13 of tubular member 11. The helical snare also helps maintain the longitudinal orientation of the foreign body for retrieval through and withdrawal from the vascular system of the patient.

As depicted in FIGS. 1 and 2, elongated tubular member 11 comprises a radiopaque plastic material tube with an overall length of approximately 100 cm. Distal portion 25 of the tube comprises, for example, a commercially available polyamide material such as medical grade nylon that is approximately 6 cm in length with an outside diameter of approximately 0.054" and an inside diameter of approximately 0.036". Side ports 16 and 20 approximately 0.020" in diameter are positioned longitudinally apart approximately 18 mm and at an angle 24 toward each other of approximately 45 degrees with respect to the longitudinal axis of the tube. Side port 20 is positioned approximately 4 mm from rounded distal end 13 of the tube. A commercially available radiopaque marker paste 22 is positioned around the tube approximately half way between side ports 16 and 20 for radiographic positioning of the maximum radial opening of the helical snare loop 19. Distal portion 25 of the tube is thermally bonded in a well-known manner to proximal portion 27 using commercially available molding equipment such as PRIF process equipment from Sebra Co., Tucson, Arizona.

Proximal portion 27 of tubular member 11 is approximately 95 cm in length with a outside diameter of 0.066" and an inside diameter of 0.042". A stainless steel wire braid 29 is embedded as a torque control member in the wall of the tube during extrusion thereof.

Filament wire 17 is a stainless steel wire approximately 100 cm in length with an 0.018" diameter along proximal portion 35. Distal portion 34 of the wire is approximately 15 cm in length and has a 0.0065" diameter, which is tapered and center ground from proximal portion 35 for approximately 4–5 cm. The distal portion of the wire is inserted into the proximal end of tubular member passage 14 and out tube wall 23 through side port 16. Distal portion 34 of the filament wire is helically wrapped once around exterior surface 15 of the tubular member in a clockwise direction and inserted back into passage 14 through side port 20. The distal end of the wire is then extended out the distal end of passage 14. A radiopaque marker 21 is force fit into passage 14 approximately 2-3 mm from distal end 13 of the tube for radiographic visualization thereof. The radiopaque marker is, for example, a sleeve of a radiopaque metal such as platinum, iridium, or tungsten approximately 0.030" in length with an outside diameter of 0.040" and an inside diameter of 0.032". Distal end 18 of the filament wire is passed through the metal sleeve and wound into a coil with several turns. The coil is soldered closed to prevent the wire from being pulled back through the radiopaque metal marker sleeve. Coiled and soldered distal end 18 of the filament wire is positioned adjacent the metallic sleeve with distal end 13 of the tubular member being thermally molded into an atraumatic rounded shape.

With distal portion 34 of the filament wire helically wrapped around exterior surface 15 of the tubular member between side ports 16 and 20, the combined outer diameter or cross-sectional dimension of the filament wire and tubular member distal portion 25 approximates the outer diameter or cross-sectional dimension of proximal portion 27 of the tubular member. Sizing the combined diameter of the collapsed helical snare loop and distal portion 25 of the tubular member to approximate the outside diameter of proximal portion 27 of the tubular member minimizes trauma to the vascular system during introduction of the helical surgical snare to the foreign body.

Depicted in FIG. 3 is a partially sectioned end view of helical surgical snare 10 and foreign body 26 of FIG. 2 taken along the line 3—3. Helical snare loop 19 more clearly depicts open position 36 of the loop with foreign body 26 positioned therein. To capture foreign body 26 against exterior surface 15 of tubular member 11, distal portion 34 of filament wire 17 is pulled into side port 16 with the aid of handle 30.

Depicted in FIG. 4 is an enlarged and partially sectioned bottom view of distal portion 25 of tubular member 11 with foreign body 26 positioned against exterior surface 15 with helical snare loop 19 in partially collapsed position 28.

Depicted in FIG. 5 is an end view of elongated tubular member 11 and captured foreign body 26 of FIG. 4 taken along the line 5—5. Captured foreign body 26 is positioned against exterior surface 15 of the tubular member with helical snare loop 19 in partially collapsed position 28. As depicted, captured foreign body 26 is in substantial parallel alignment with the longitudinal axis of tubular member 11 to facilitate withdrawal of the tubular member and captured foreign body with a minimum of trauma to the vascular system.

Depicted in FIG. 6 is an enlarged and partially sectioned top view of helical surgical snare 10 of FIG. 1 and, in particular, proximal end 12 of tubular member 11 with handle 30 connected thereto. Extending through passage 14 of elongated tubular member 11 is filament wire 17 with cannula 37 connected to the proximal end thereof. For example, cannula 37 is a 21 gauge, regular wall stainless steel tube approximately 14 cm in length with an outside diameter of 0.032" and an inside diameter of 0.020". With the helical snare loop in a fully collapsed position, approximately 10.6 cm of the filament wire is extended out the tapered end of proximal end 12 of tubular member 11. Cannula 37 is positioned over the proximal end of the wire and soldered thereto. The cannula is connected to finger handle piece 32 via 0-ring seal 38 and through the longitudinal through passage of side port connector 33. Stationary thumb handle piece 31 is connected to the proximal end of the tubular member via side port connector 33 and intermediate connector 39. The side arm of side port connector 33 facilitates the injection of contrast medium into the vascular system of the patient via passage 14 and side ports 16 and 20 of tubular member 11. O-ring seal 38 prevents the contrast medium from leaking out the proximal end of the tube around cannula 37. Operation of helical snare loop 19 is again facilitated by the slidable movement of finger handle piece 32 relative to stationary handle piece 31.

It is to be understood that the above-described helical surgical snare is merely an illustrative embodiment of the principles of this invention and that other snares may be devised by those skilled in the art without departing from the spirit and scope of this invention. In particular, side ports 16 and 20 have been longitudinally spaced apart along a line parallel to the longitudinal axis of elongated tubular member 11. As a result, helical snare loop 19 is formed with its apex being diametrically positioned on the opposite side of the catheter in alignment with radiopaque marker 22, which is positioned midway between the side ports. The apex of the surgical snare loop can be repositioned by altering the longitudinal alignment of side ports 16 and 20 along the circumference of the tubular member. The inclination of the side ports with respect to the longitudinal axis of the tubular member can also be varied to affect the longitudinal placement of the loop apex between the two side ports. Although this preferred embodiment has been described with respect to use in the vascular system of a patient, other parts and systems of the body such as the biliary and urinary systems can be accessed by this helical snare to retrieve or reposition medical devices or fragments thereof. Use of this snare is also contemplated during open or minimally invasive surgical procedures.

What is claimed is:

1. A helical surgical snare (10) comprising:
   an elongated member (11) having a proximal end (12), a distal end (13), a passage (14) extending longitudinally therein, an exterior surface (15), and a first side port (16) positioned in said exterior surface proximate said distal end and communicating externally and with said passage; and
   a filament (17) extending through and movable within said passage and said first side port, having a distal end (18) attached to said elongated member, being wrapped around said exterior surface and forming a helical snare loop (14) external to said elongated member, said loop opening when said filament is moved through said first side port and away from said exterior surface of said elongated member, said loop closing when said filament is moved through said first side port and toward said exterior surface of said elongated member.

2. The snare of claim 1 wherein said elongated member further includes a second side port (20) positioned distally from said first side port and communicating externally and with said passage and wherein said filament also extends through said second side port and is wrapped around said exterior surface of said elongated member between said first and said second side ports.

3. The snare of claim 2 wherein said distal end of said filament is in said passage attached to said distal end of said elongated member.

4. The snare of claim 3 further comprising a radiopaque marker (21) positioned at said distal end of said filament.

5. The snare of claim 3 further comprising a radiopaque marker (22) on said elongated member positioned between said first and said second side ports.

6. The snare of claim 2 wherein said first and said second side ports are inclined through a wall of said elongated member at a predetermined angle (24).

7. The snare of claim 1 wherein said elongated member further includes a distal portion (25) having a cross-sectional dimension and a proximal portion (27) having a cross-sectional dimension greater than said cross-sectional dimension of said distal portion.

8. The snare of claim 7 wherein said loop around said elongated member has a collapsed position (28) against said exterior surface and wherein a combined cross-sectional dimension of said distal portion of said elongated member and said filament with said loop in said collapsed position approximate said cross-sectional dimension of said proximal portion of said elongated member.

9. The snare of claim 7 wherein said proximal portion of said elongated member includes a torque control member (29).

10. The snare of claim 9 wherein said torque control member comprises a wire braid positioned in a wall of said elongated member.

11. The snare of claim 1 further comprising a handle (30) connected to a proximal end of said filament and said proximal end of said elongated member.

12. The snare of claim 11 wherein said handle includes a first piece (31) connected to said proximal end of said elongated member and a second piece (32) connected to said proximal end of said filament and moveable with respect to said first piece when moving said filament in said passage of said elongated member.

13. The snare of claim 11 further comprising a side port connector (33) positioned proximate said proximal end of said elongated member and communicating with said passage of said elongated member.

14. The snare of claim 1 wherein said filament includes a distal portion (34) having a cross-sectional dimension and a proximal portion (35) having a cross-sectional dimension greater than said cross-sectional dimension of said distal portion.

15. A helical surgical snare (10) comprising:
an elongated tubular member (11) having a proximal end (12), a distal end (13), a passage (14) extending longitudinally therein, an exterior surface (15), and a first (16) and a second side port (20) positioned longitudinally apart in said exterior surface proximate said distal end and communicating externally and with said passage; and
a filament wire (17) extending through and moveable within said passage and at least one of said first and second side ports, having a distal end (18) attached to said elongated tubular member, being helically wrapped around said exterior surface between said first and second side ports and forming a helical snare loop (19) external to said elongated member, said snare loop having an open (36) and a collapsed (28) position.

16. The snare of claim 15 wherein said distal end of said filament wire is attached in said passage to said distal end of said elongated tubular member.

17. The snare of claim 15 wherein said elongated tubular member further includes a distal portion (25) having a cross-sectional dimension and a proximal portion (27) having a torque control member (29) and a cross-sectional dimension greater than said cross-sectional dimension of said distal portion.

18. The snare of claim 15 wherein said loop in said collapsed position is against said exterior surface and wherein a combined cross-sectional dimension of said distal portion of said elongated member and said filament wire with said loop in said collapsed position approximates said cross-sectional dimension of said proximal portion of said elongated member.

19. The snare of claim 15 wherein said filament wire includes a distal portion (34) having a cross-sectional dimension and a proximal portion (35) having a cross-sectional dimension greater than said cross-sectional dimension of said distal portion.

20. A helical surgical snare comprising:
an elongated tubular member (11) having a proximal end (12), a distal end (13), a passage (14) extending longitudinally therein, an exterior surface (15), a distal portion (25) having a diameter, a proximal portion (27) having a braided wire (29) therein and a diameter greater than said diameter of said distal portion, and a first (16) and a second (20) side port positioned longitudinally apart in said exterior surface proximate said distal end and communicating externally and with said passage;
a filament wire (17) extendable through and moveable within said passage and at least one of said first and second side ports, a distal portion of said filament wire (34) having a diameter and a distal end (18) attached to said elongated tubular member, a proximal portion of said filament wire (35) having a diameter greater than said diameter of said distal portion of said filament wire, being helically wrapped around said exterior surface between said first and second side ports and forming a helical snare loop (19) external to said elongated tubular member, said helical snare loop having an open (36) and a collapsed (28) position;
a first handle piece (31) connected to a proximal end of said elongated tubular member; and
a second handle piece (32) connected to said proximal end of said filament wire and movable with respect to said first handle piece for moving said filament wire in said passage of said elongated tubular member.

* * * * *